United States Patent [19]

Shackelford et al.

[11] Patent Number: 4,670,141

[45] Date of Patent: * Jun. 2, 1987

[54] METHOD AND APPARATUS FOR FACILITATING COMPRESSION OF PACKING MATERIAL IN A LIQUID CHROMATOGRAPHY COLUMN

[75] Inventors: Carl L. Shackelford, San Pablo; Kenneth Rainin, Piedmont, both of Calif.

[73] Assignee: Rainin Instrument Co., Inc., Emeryville, Calif.

[*] Notice: The portion of the term of this patent subsequent to Nov. 5, 2002 has been disclaimed.

[21] Appl. No.: 742,265

[22] Filed: Jun. 7, 1985

Related U.S. Application Data

[63] Continuation-in-part of Ser. No. 584,611, Feb. 29, 1984, Pat. No. 4,551,250.

[51] Int. Cl.⁴ .............................................. B01D 15/08
[52] U.S. Cl. .................................. 210/198.2; 210/656; 55/386
[58] Field of Search ................. 210/656, 198.2; 55/386

[56] References Cited

U.S. PATENT DOCUMENTS 4,470,910  9/1984  Quemerais et al. ................. 210/656

Primary Examiner—Ernest G. Therkorn
Attorney, Agent, or Firm—Townsend and Townsend

[57] ABSTRACT

A liquid chromatography column apparatus which utilizes sorbent packing material in a tube having a first end portion and a second end portion. The first end portion of the tube includes a plug having a passage therethrough. The plug fits in the tube adjacent the packing material and is movable within the tube. An end fitting is also employed adjacent the plug. The end fitting has a passage therethrough which communicates with the passage of the plug. A seal is used inside the tube between the tube and the end fitting. The second end portion of the tube is enclosed and also includes a passage from the interior to the exterior of the tube. A manually actuable gear mechanism is incorporated in the end fitting of the first end portion of the tube for facilitating application of axial force to the packing material, thereby compressing the packing material so as to eliminate voids and channels in the packing material. Other features are also disclosed.

20 Claims, 6 Drawing Figures

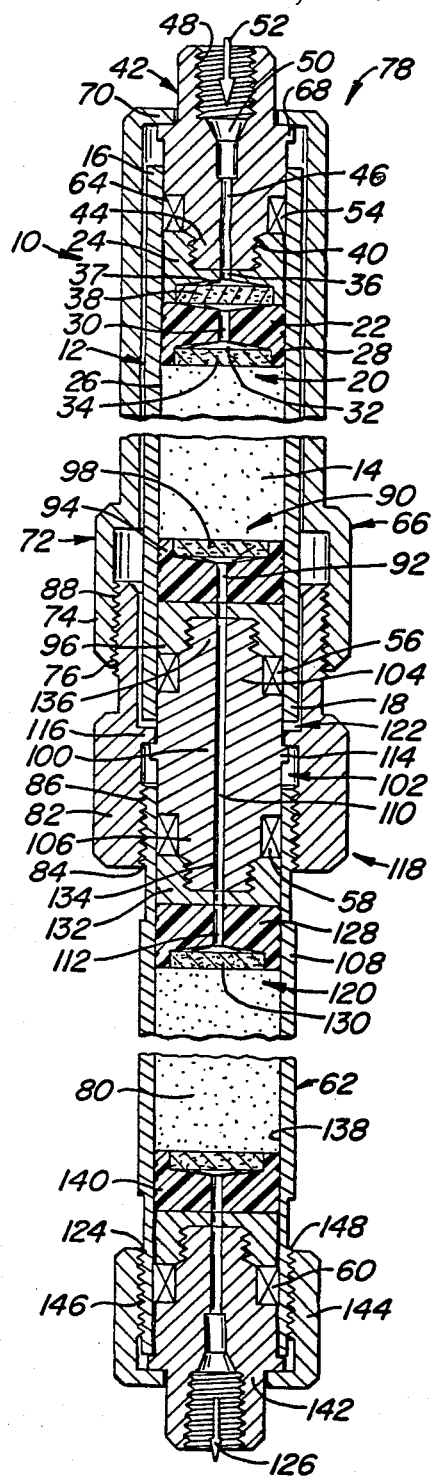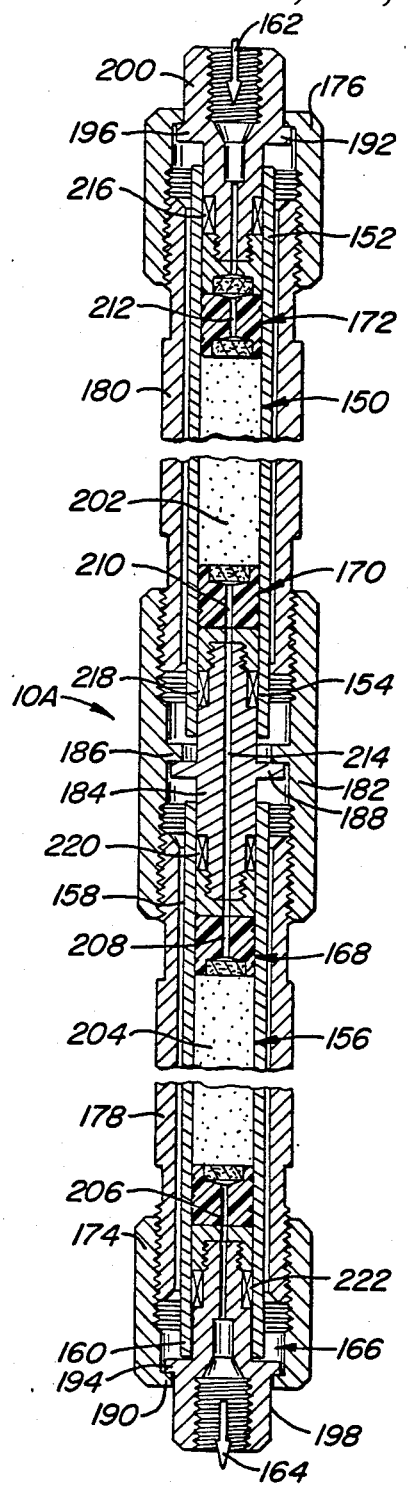
FIG._1.　　FIG._2.

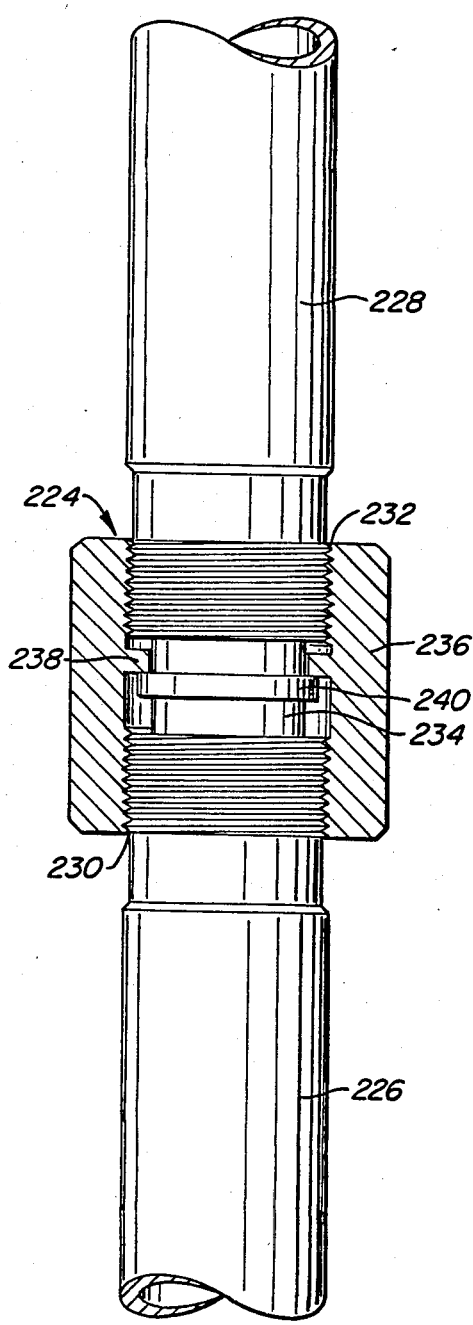
FIG._3.
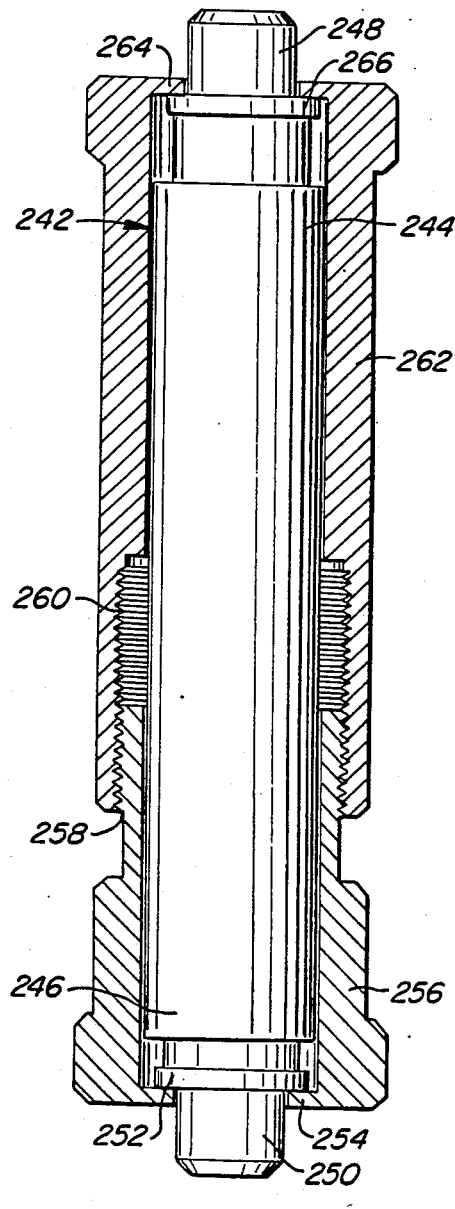
FIG._4.

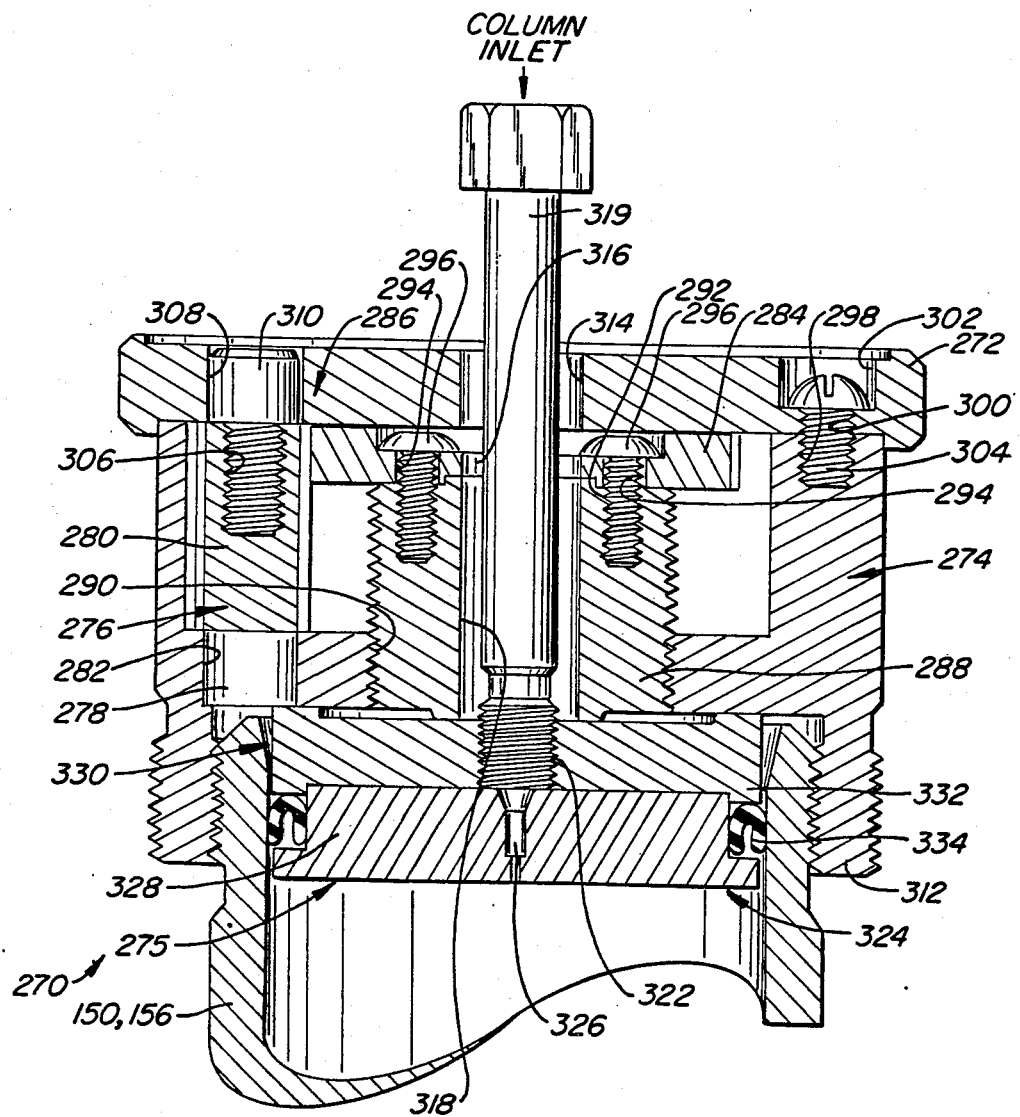
FIG._5.

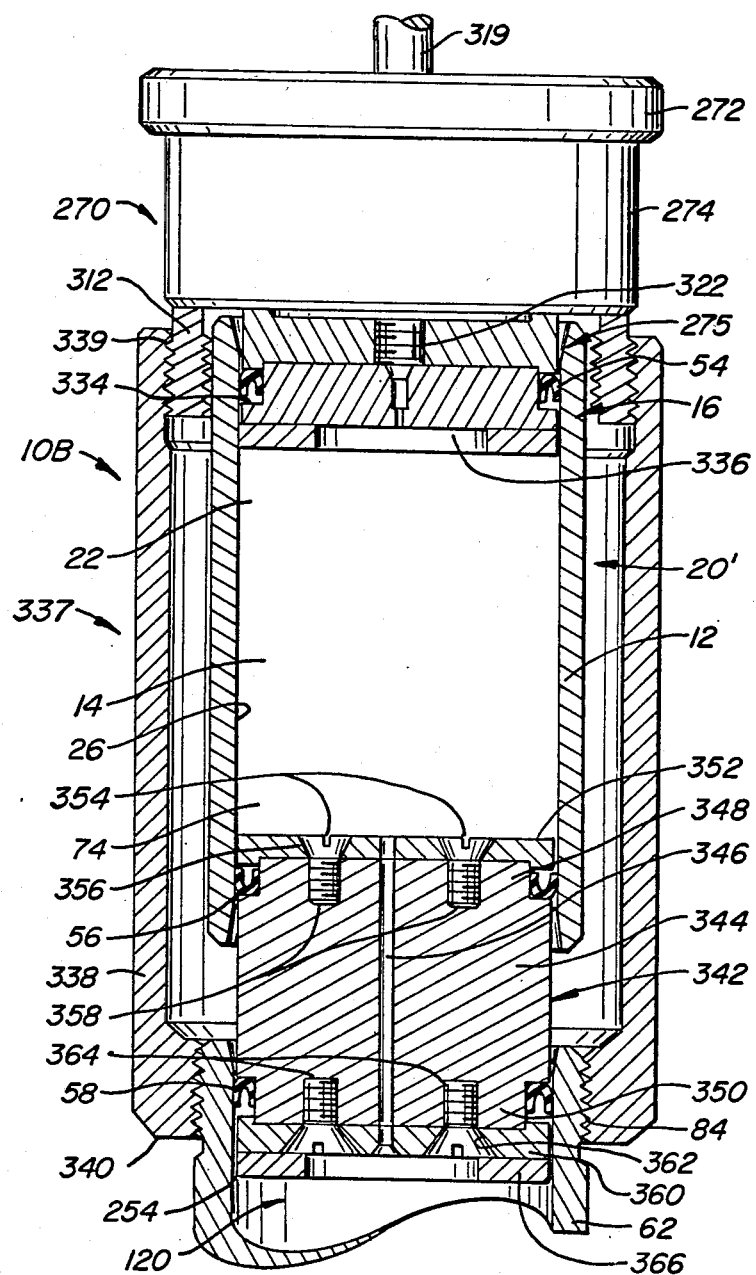
FIG._6.

METHOD AND APPARATUS FOR FACILITATING COMPRESSION OF PACKING MATERIAL IN A LIQUID CHROMATOGRAPHY COLUMN

CROSS-REFERENCE TO RELATED APPLICATIONS

This is a continuation-in-part of a patent application of Carl L. Shackelford and Kenneth Rainin, entitled "MODULAR LIQUID CHROMATOGRAPHY COLUMN APPARATUS," Ser. No. 584,611, filed on Feb. 29, 1984, now U.S. Pat. No. 4,551,250, and assigned to the same assignee as this application.

BACKGROUND OF THE INVENTION

This invention relates to liquid chromatography equipment and, more particularly, to liquid chromatography column apparatus which preferably has a modular structure, useful in analytical semi-preparative and preparative liquid chromatography separation processes. Specifically, the invention is directed to a novel and useful method and apparatus for facilitating application of compressional force on the bed of sorbent packing material within liquid chromatography column apparatus.

High pressure liquid chromatography techniques utilize pumps which have a pressure pulsation as a delivery characteristic. This pulsation has a tendency to disturb sorbent packing material in a liquid chromatography column. In particular, a void may develop at the top or head of the column. Also, "channels" may develop at the interface of the packing material and the column wall. This deterioration is exacerbated by chemical attack, high temperatures, and other factors. In this regard, the initial packing of a column may also create discontinuities in a portion of the packing material.

On the one hand, known liquid chromatography systems, such as the liquid chromatography systems disclosed in U.S. Pat. Nos. 4,283,280 and 4,313,828, do not apply pressure to the packing material while maintaining seal integrity. On the other hand, the liquid chromatography column apparatus disclosed in the copending patent application of Carl L. Shackelford and Kenneth Rainin, entitled "MODULAR LIQUID CHROMATOGRAPHY COLUMN APPARATUS," Ser. No. 584,611, filed on Feb. 29, 1984, now U.S. Pat. No. 4,551,250, and assigned to the same assignee as this application, discloses a modular liquid chromatography column apparatus which applies pressure to the packing material while maintaining seal integrity. Pressure is applied to the packing material by tightening an axial compression nut threadably connected with a threaded column tube such that an axial compression piston axially disposed within the axial compression nut is forced against a movable bed retainer in contact with sorbent packing material contained within the tube for compressing the packing material.

The modular liquid chromatography column apparatus disclosed in the aforementioned patent application of Shackelford and Rainin, Ser. No. 584,611, filed on Feb. 29, 1984, now U.S. Pat. No. 4,551,250, operates effectively for compressing the packing material while maintaining seal integrity in various sizes of modular liquid chromatography column apparatus having tubes with inside diameters of approximately 21.4 millimeters or less. In the case of modular liquid chromatography column apparatus having tubes with larger inside diameters, for example, 41.4 millimeters, the surface area of the top or head of the sorbent packing material is much larger and requires significantly more force for compressing the packing material so as to eliminate undesired voids and channels than in the case of the smaller modular liquid chromatography column apparatus. In order to apply sufficient pressure for compressing the packing material, large wrenches are needed for tightening the end fittings on the tubes in a manner similar to the technique used for effecting a tight seal disclosed in U.S. Pat. Nos. 4,283,280 and 4,313,828. This eliminates the advantageous feature of being able to hand tighten the end fittings of liquid chromatography column apparatus for compressing the packing material.

A liquid chromatography system which solves the hereinabove mentioned problem would be a great advance in the field of liquid chromatography equipment.

SUMMARY OF THE INVENTION

In accordance with this invention, a novel and useful liquid chromatography column apparatus is provided which solves the problem encountered in compressing the packing material in liquid chromatography column apparatus. The invention is particularly advantageous when incorporated in modular liquid chromatography column apparatus, especially modular liquid chromatography column apparatus having a relatively large diameter column. In accordance with one embodiment of the invention, compressing means in the form of a manually actuable gear mechanism is incorporated in the end fitting of the liquid chromatography column apparatus for facilitating application of axial force to plugging or enclosing means in order to drive the plugging or enclosing means against the packing material, thereby compressing the packing material so as to eliminate voids and channels in the packing material.

The liquid chromatography column apparatus of the invention employs a tube, which can be a first tube, filled with sorbent packing material used for separating constituents. The tube has a first end portion and second end portion. Means is provided for plugging the first end portion of the tube and is placed adjacent the packing material. The plugging means includes a passage therethrough which serves as an inlet to the packing material for the solution being analyzed. The plugging means is movable within the tube and is therefore capable of pressing against the packing material. The plugging means can take the form of a stopper which is movable within the tube and a seal retainer adjacent the stopper. Both the seal retainer and stopper can include passages therethrough for transfer of the solution from the exterior of the tube to the packing material. The stopper and seal retainer can include filters which aid in filtering the solution being analyzed before contact with the packing material in the tube. Such filters also tend to properly distribute the solution across the head of the packing material.

The column apparatus also includes an end fiting, which can be a first end fitting, having a portion placed within the tube adjacent the plugging means. The end fitting includes a passage therethrough which connects to the passage of the plugging means, namely, the passages of the stopper and seal retainer.

The column apparatus further includes means for sealing a portion of the inside of the tube between the plugging means and the end fitting. The sealing means can lie between the seal retainer and the end fitting and can be movable along the inside of the tube. Such movement can take place in conjunction with the movable stopper and seal retainer. The end fitting can threadably engage a threaded portion of the seal retainer. The second end portion of the tube is enclosed by appropriate enclosing means having a passage therethrough which serves as an outlet of the tube.

In accordance with the invention, compressing means is incorporated into the end fitting for applying axial force to the plugging means, which moves the plugging means against the packing material. The compressing means permits pressure to be exerted against the packing material by the plugging means and also effects operation of the sealing means to prevent leakage of the solution from inside the tube. In accordance with one embodiment of the invention, the compressing means comprises a manually actuable gear means incorporated into the end fitting for applying axial force to the plugging means, thereby compressing the packing material.

A second tube can be used in conjunction with the first tube. The second tube can be filled with packing material and have a first end portion and a second end portion. Each end portion of the second tube can include means for enclosing the second tube. A coupler element interconnects the first and second tubes. The coupler element includes a first portion and a second portion such that the first portion fits within and is movable within the second end portion of the first tube. Similarly, the second portion of the coupler element fits within and is movable within the first end portion of the second tube. The second tube has a structure which provides first and second passages through first and second enclosing means, respectively, which communicate with packing material in the second tube. The coupler element also is provided with a passage therethrough which communicates with the passage of the enclosing means of the second end portion of the first tube and with the first passage of the first enclosing means of the first end portion of the second tube. The coupler element can also include means for holding the first and second portions of the coupler element to the enclosing means of the second end portion of the first tube and to the first enclosing means of the first end portion of the second tube, respectively.

In accordance with the invention, compressing means is incorporated into the end fitting for applying axial force to the plugging means, as well as to the coupler element, which moves the coupler element against the enclosing means of the second end portion of the first tube. The compressing means permits pressure to be exerted against the packing material by both the plugging means and enclosing means of the second end portion of the first tube.

The compressing means in accordance with the invention can alternatively be connected to an end fitting of the second end portion of the second tube for applying axial force to the end fitting of the second end portion of the second tube, which moves the end fitting of the second end portion of the second tube against the enclosing means of the second end portion of the second tube. In effect, the plugging means and enclosing means of the first and second tubes are squeezed toward one another creating pressure on the packing material within the first and second tubes.

The invention provides a novel and useful compressing means for a liquid chromatography column apparatus, especially a modular liquid chromatography column apparatus, which can be a high performance or high pressure liquid chromatography column (HPLC) apparatus. The invention provides a liquid chromatography column apparatus which can be hand tightened and loosened without the need for large wrenches and which provides for reusing end fittings supplied for this purpose. The invention provides a liquid chromatography column apparatus which applies pressure directly to the packing material within the column to correct any voids or channels which may be present in the column after the initial packing or which may develop after use of the column apparatus. The invention provides a liquid chromatography column apparatus which possesses a relatively small dead volume. The invention provides a liquid chromatography column apparatus which permits the coupling of a pre-column or guard column to a separation column or the coupling of a plurality of separation columns together and provides for the application of mechanical pressure to the packing material in all columns.

The present invention provides a liquid chromatography column apparatus which accommodates incorporation of seals and filters within the tubular bodies of the column apparatus. The invention provides a liquid chromatography column apparatus which accommodates a replaceable filter element within a packed column that prevents fouling and early disposal of the column. The invention provides a liquid chromatography column apparatus which minimizes the need for peripheral hardware, thereby reducing the overall cost of the column apparatus.

BRIEF DESCRIPTION OF THE DRAWINGS

The above and other features and the concomitant advantages of the present invention will be better understood and appreciated by those skilled in the art in view of the description of the preferred embodiments given below in conjunction with the accompanying drawings. In the drawings:

FIG. 1 is a sectional view having broken portions of an embodiment of liquid chromatography column apparatus;

FIG. 2 is a sectional view having broken portions of an alternative embodiment of liquid chromatography column apparatus;

FIG. 3 is a sectional view partially in elevation showing a coupling of two tubes;

FIG. 4 is a sectional view partially in elevation showing a single packed tube, the packing material of which can be axially compressed;

FIG. 5 is a sectional view having broken portions of an embodiment of compressing means in accordance with the invention; and FIG. 6 is a sectional view partially in elevation showing another alternative embodiment of liquid chromatography column apparatus.

DESCRIPTION OF THE PREFERRED EMBODIMENTS

Various aspects of the present invention will evolve from the following detailed description of the preferred embodiments which should be referenced to the hereinabove described drawings.

By way of background, liquid chromatography column apparatus as a whole is shown in the drawings by reference characters 10 and 10A. The column apparatus 10 shown in FIG. 1 includes a tube 12 which is filled with packing material 14 typically used in liquid chromatography separations, for example, silica gel, and the like. Tube 12 can be constructed of relatively rigid material, such as stainless steel, aluminum, and the like. Tube 12 includes a first end portion 16 and a second end portion 18.

Means 20 is provided for plugging first end portion 16 of tube 12. Plugging means 20 can include a stopper 22 and a seal retainer 24 in end-to-end configuration. Both stopper 22 and seal retainer 24 are movable along the inside surface 26 of tube 12. Stopper 22 can exert pressure on packing material 14 by direct contact.

Stopper 22 can be constructed of a plastic material and include a series of grooves or striations 28 on its outer surface. A passage 30 also exists to allow liquid to travel therethrough. Passage 30 flares into an open chamber 32 in stopper 22, which contains a filter 34 in the form of a frit which filters and distributes liquid passing therethrough.

Seal retainer 24 includes a passage 36 and an open chamber 37 which holds a frit filter 38 adjacent stopper 22. Filter 38 is easily replaceable. Seal retainer 24 can be constructed and formed of metallic material, such as stainless steel, aluminum, and the like.

An end fitting 42 includes a threaded protrusion 44 which threadably engages a threaded hollow 40 of seal retainer 24. Thus, seal retainer 24 and end fitting 42 can be locked together as a unit. End fitting 42 also includes a threaded opening 48 connected through a reducing chamber 50 and a passage 46 to passage 36 of seal retainer 24. Thus, liquid being analyzed by column apparatus 10 flows according to arrow 52.

Leakage from the inside of tube 12 is controlled by seals 54 and 56 (shown schematically). A second tube 62, which will be more fully described hereinafter, utilizes seals 58 and 60. Seals 54, 56, 58, and 60 can be a spring loaded Teflon and Teflon compounded seal manufactured under the name "BAL-SEAL" by the Bal-Seal Engineering Company of Santa Ana, Calif., Series U-300 for static conditions. Seal 54 seals a portion of the inside surface 26 of tube 12 between plugging means 20 and end fitting 42. By way of example, seal 54 occupies a toroidal chamber 64 formed by end fitting 42, seal retainer 24, and the inside surface 26 of tube 12.

FIG. 1 also depicts means 66 for retaining end fitting 42 within tube 12. Retaining means 66 can take the form of a rim 68 on end fitting 42 which contacts a collar 70 of coupling means 72 for linking tube 12 to a second tube 62. Coupling means 72 can take the form of a generally cylindrical member 74 having a threaded end portion 76, as well as the heretofore described collar 70.

Column apparatus 10 also includes means 78 for urging end fitting 42 against plugging means 20. Urging means 78 creates axial compression along tubes 12 and 62, which in turn compresses packing material 14 in tube 12 and packing material 80 in second tube 62. Urging means 78 combines coupling means 72 with an end cap 82 and a threaded first end portion 84 of second tube 62. An internally threaded portion 86 of end cap 82 threadably engages threaded first end portion 84 of tube 62. In addition, an externally threaded portion 88 of end cap 82 threadably engages the threaded end portion 76 of cylindrical member 74.

Tube 12 possesses means 90 for enclosing second end portion 18. Enclosing means 90 includes a passage 92 therethrough to permit flow of liquid from packing material 14. As shown in FIG. 1, enclosing means 90 includes a stopper 94 and a seal retainer 96 positioned adjacent to one another and movable along the inside surface 26 of tube 12. Stopper 94 includes a frit filter 98. Stopper 94 can be of similar construction to stopper 22.

Column apparatus 10 includes a coupler or coupler means 100 for connecting tube 12 in fluid communication with second tube 62 and for maintaining axial compression of packing material 14 and 80 in tube 12 and second tube 62, respectively. Coupler 100 can include an element 102 which has a first portion 104 and a second portion 106. First portion 104 and second portion 106 of element 102 fit within second end portion 18 of tube 12 and first end portion 108 of second tube 62, respectively. Thus, forces exerted by urging means 78 are received by element 102. Element 102 also provides a portion of the chambers which house seals 56 and 58 of tube 12 and second tube 62, respectively. Element 102 is structured to include a passage 110 therethrough which communicates with passage 92 of enclosing means 90 and a passage 112 found in second tube 62 which will be discussed hereinafter.

A ring 114 of element 102 provides a place of contact with a ring 116 of end cap 82. These contacting rings 114 and 116 in conjunction with the threaded engagement between end cap 82 and threaded first end portion 84 of second tube 62 result in means 118 for urging element 102 against enclosing means 120 of first end portion 108 of second tube 62. In addition, the threaded connection between end cap 82 and cylindrical member 74 functions as means 122 for retaining element 102 within second end portion 18 of tube 12 and the first end portion 108 of second tube 62.

Again, with reference to FIG. 1, second tube 62 is constructed with first end portion 108 and a second end portion 124. Packing material 80 fills the inside of second tube 62. First end portion 108 of second tube 62 includes enclosing means 120 having passage 112 therethrough which has been previously described. Enclosing means 120 can externalize in a stopper 128 having a frit filter 130 on the packing side thereof. Stopper 128 can be of similar construction to stopper 22.

A seal retainer 132 threadably engages a threaded boss 134 of second portion 106 of element 102. Likewise, a threaded boss 136 of first portion 104 of element 102 threadably engages seal retainer 96 found in second portion 18 of tube 12. Stopper 128 and seal retainer 132 are movable along the inside surface 138 of second tube 62.

Second end portion 124 of second tube 62 also includes enclosing means 140 which will not be described in detail since it is essentially identical to enclosing means 120 of first end portion 108 of second tube 62, with its elements being in reverse order.

An end fitting 142 and enclosing means 140 are held within second tube 62 by an end cap 144. A threaded portion 146 of end cap 144 threadably engages a threaded second end portion 148 of second tube 62 to achieve this end.

Second tube 62 can alternatively be fitted within components similar to end fitting 142 and end cap 144 at its first end portion 108, with the elements being in reverse order. Thus, a column would be formed having axial compression exerted by tightening end cap 144 and another end cap similar to end cap 144 at second end portion 124 and first end portion 108 of second tube 62. Such compression compresses packing material 80 in the middle portion of second tube 62.

Turning to FIG. 2, another embodiment 10A of column apparatus is depicted. Column apparatus 10A includes a first tube 150 having a first end portion 152 and a second end portion 154. A second tube 156 is also provided having a first end portion 158 and a second end portion 160. Liquid is intended to flow through column apparatus 10A starting at inlet arrow 162 and exiting at outlet arrow 164.

Referring to FIG. 1 and with reference to the enclosing means 140 of the second end portion 124 of second tube 62, it can be seen that a similar enclosing means 166 is included in second end portion 160 of second tube 156 shown in FIG. 2. Similarly, enclosing means 120 of first end portion 108 of second tube 62 is similar to enclosing means 168 for first end portion 158 of tube 156. Enclosing means 90, plugging means 20, and end fitting 42 of tube 12 are also comparable to enclosing means 170 and 172 of first tube 150 and an end fitting 200, respectively.

It can be observed that tubes 150 and 156 are of a smaller diameter than tubes 12 and 62 of FIG. 1. Also, tubes 150 and 156 both include externally threaded portions. End caps 174 and 176 threadably engage bushings 178 and 180, respectively. A bushing 182 threadably engages bushings 178 and 180.

A coupling element 184 extends into tubes 150 and 156 and threadably engages enclosing means 168 and 170. An internal flange 186 of bushing 182 contacts a ring 188 of coupling element 184 to urge the same toward second tube 156. End caps 174 and 176 also include respective collars 190 and 192 which engage flanges 194 and 196 of end fittings 198 and 200, respectively. Since enclosing means 166, 168, 170, and 172 are movable along the inside surfaces of tubes 150 and 156, the tightening of one of end caps 174 and 176 or bushing 182 will cause axial compression along tubes 150 and 156. Such compression will also exert a force on packing material 202 and 204 of tubes 150 and 156.

Passages 206, 208, 210, and 212 of enclosing means 166, 168, 170, 172, respectively, permit the flow of liquid being analyzed to the packing material 202 and 204. In addition, passage 214 of coupling element 184 links the flow of liquid between first tube 150 and second tube 156.

Turning to FIG. 3, coupling means 224 is illustrated for the purpose of connecting tubes 226 and 228. Tubes 226 and 228 include threaded end portions 230 and 232, respectively, similar to threaded first end portion 84 of second tube 62 shown in FIG. 1. A coupler element 234 extends into the interior of tubes 226 and 228 much in the same manner as coupler 100 extends into tubes 12 and 62 in FIG. 1. A bushing 236 possesses an internal ring 238 which engages a ring 240 around coupler element 234. Tubes 226 and 228 can include enclosing means similar to enclosing means 120 of the first end portion 108 of second tube 62 in abutment with either end of coupler element 234. A similar enclosing means can also be provided at the other ends of tubes 226 and 228 (not shown).

Turning to FIG. 4, a single tube 242 is depicted having unthreaded first and second end portions 244 and 246. End fittings 248 and 250 partially fit within first and second end portions 244 and 246, respectively, and are similar in construction to end fitting 42 associated with tube 12 shown in FIG. 1. Also, enclosing means such as enclosing means 172 of first end portion 152 of tube 150 shown in FIG. 2 can be found within tube 242 at first and second end portions 244 and 246. Tube 242 is filled with packing material such as packing material 202 which is found within tube 150 shown in FIG. 2.

A rim 252 of end fitting 250 is engaged by a flange 254 of an end cap 256. End cap 256 also includes a threaded portion 258 which is threadably engaged by a threaded portion 260 of an end cap 262. A flange 264 of end cap 262 engages a rim 266 of end fitting 248. Thus, tightening end caps 256 and 262 will cause end fittings 248 and 250 to compress the packing material (not shown) within tube 242.

In operation, the user connects tube 12 to second tube 62 shown in FIG. 1 by use of coupler 100. Plugging means 20 and enclosing means 90, 120, and 140 on both ends of tubes 12 and 62 are inserted. End cap 144 and cylindrical member 74 are tightened against end fittings 142 and 42, respectively, to compress the items found within tubes 12 and 62. Liquid is directed into column apparatus 10 according to directional arrow 52 and exits from the same toward a directional arrow 126. Separation of the components of the liquid takes place within the packing material 14 and 80 of tubes 12 and 62, respectively.

Similarly, column apparatus 10A is assembled and tightened using end caps 174 and 176 and bushing 182. Liquid is then directed according to directional arrow 162 into column apparatus 10A and exits at directional arrow 164. Again, separation takes place in packing material 202 and 204 of tubes 150 and 156, respectively.

The exertion of axial compression in either the embodiment 10 shown in FIG. 1 or 10A shown in FIG. 2 will also effect the sealing of the tubes. For example, tubes 12 and 62 are sealed against leakage from within at seals 54 and 56 and at seals 58 and 60, respectively. Column apparatus 10A seals tubes 150 and 156 at seal areas 216, 218, 220, and 222 (shown schematically). Seals employed in column apparatus 10A are similar to those employed in column apparatus 10. The tightening hereinabove described can be without the use of tools; in other words, the column apparatuses 10 and 10A can be hand tightened. It has been found that liquids under a pressure in excess of six thousand pounds per square inch (422 kg. per square centimeter) flow through the column apparatus 10 or 10A without leakage therefrom.

It is also possible to link other columns or tubes to the two column embodiment shown in FIGS. 1 and 2. For example, FIG. 3 represents the linking of two tubes 226 and 228 together. By merely substituting tube 62 for tube 228, three tubes can be linked together in series, namely, tubes 12, 62, and 226. This may be desirable in certain liquid chromatography separation processes.

With reference to FIG. 4, it can be seen that a single tube, which may be a pre-column or guard column, also enjoys axial compression of the packing material therewithin. By simply tightening end caps 256 and 262, such axial compression is effected. It should be noted that the sealing described in detail with reference to FIGS. 1 and 2 also takes place in the embodiments shown in FIGS. 3 and 4.

In accordance with the present invention, compressing means 270 is preferably incorporated into column apparatus 10 shown in FIG. 1, column apparatus 10A shown in FIG. 2, the column apparatus partially depicted in FIG. 3, or the column apparatus shown in FIG. 4. One embodiment of compressing means 270 in accordance with the invention is shown in FIG. 5. Preferably, compressing means 270 is in the form of a manually actuable gear means as shown in FIG. 5.

As shown in FIG. 5, compressing means 270 includes an end cap 272. Furthermore, compressing means 270 includes a housing 274. Compressing means 270 also preferably includes a modified seal retainer 275, as will be described in more detail later.

Compressing means 270 further includes a pinion gear 276 having a smooth cylindrical base portion 278 and a longitudinally grooved gear portion 280. Base portion 278 resides in a cylindrical bore 282 provided in housing 274 for rotation about an axis parallel to the axis of column apparatus 10, for example.

Compressing means 270 additionally includes a drive gear 284 having teeth which mesh with the teeth of pinion gear 276 at a location indicated by the numeral 286 in FIG. 5. Compressing means 270 further includes a threaded spindle 288 threadably engaged in a threaded central bore 290 of housing 274. Drive gear 284 is fixedly mounted to spindle 288. Preferably, spindle 288 is provided with threaded wells 292. Drive gear 284 is provided with bores 294. Threaded wells 292 and bores 294 are aligned, and screws 296 are inserted through bores 294 and rotated into threaded wells 292 for mounting drive gear 284 to spindle 288.

After pinion gear 276, drive gear 284, and spindle 288 are installed in housing 274, end cap 272 is secured to housing 274. Preferably, housing 274 includes at least one threaded recess 298, and end cap 272 includes at least one bore 300 having a countersink 302. Threaded recess 298 is aligned with bore 300, and a screw 304 is inserted through bore 300 and rotated into threaded recess 298 for securing end cap 272 to housing 274.

Furthermore, pinion gear 276 includes a threaded well 306. A bore 308 is provided in end cap 272 in alignment with threaded recess 306. An allen bolt 310 is inserted through bore 308 and rotated into threaded recess 306. Preferably, LOCKTITE (registered trademark) is used for sealing allen bolt 310 in threaded recess 306.

Central bores 314, 316, and 318 are provided in end cap 272, drive gear 284, and spindle 288, respectively, so that tubing 319 can be connected in fluid communication with seal retainer 275, such as by providing tubing 319 with a threaded ferrule 322 threadably secured in seal retainer 275.

As mentioned above, compressing means 270 preferably includes seal retainer 275. Seal retainer 275 includes a first element 324 having a passage 326 and a portion 328 having a reduced outside diameter. Seal retainer 275 further includes a second element 330 having a flange 332 which partially circumscribes portion 328 of first element 324, whereby a toroidal seal region 334 is formed.

Compressing means 270 can be incorporated into column apparatus 10A shown in FIG. 2 as follows. End cap 272 is substituted for end cap 174 and/or end cap 176. Housing 274 and tubing 319 are substituted for end fitting 198 and/or end fitting 200. Additionally, seal retainer 275 is substituted for the seal retainer of enclosing means 172 and/or enclosing means 166.

In operation, an allen wrench (not shown) is used for rotating allen bolt 310 so that pinion gear 276 rotates in a direction for rotating drive gear 284 to initially retract spindle 288 toward end cap 272. Next, housing 274 is grasped, and an internally threaded rim 312 is engaged with the threaded portion of bushing 180, for example. Housing 274 is then rotated by hand for tightening housing 274 onto bushing 180, for example.

Thereafter, the allen wrench (not shown) is inserted in allen bolt 310 and operated for rotating pinion gear 276 in a direction which rotates drive gear 284 in a direction for extending spindle 288 away from end cap 272. Spindle 288 engages enclosing means 172 having seal retainer 275 incorporated therein, for example, and applies axial force to enclosing means 172 such that enclosing means 172 is driven in a direction opposite the arrow 162 shown in FIG. 2. The axial force is transmitted through enclosing means 172 to packing material 202, as well as through enclosing means 170, coupling element 184, and enclosing means 168 to packing material 204, as well as through bushings 180, 182, and 178, end fitting 198, and enclosing means 166, for example, for compressing the packing material in tubes 150 and 156.

Pinion gear 276 has a diameter smaller than the diameter of drive gear 284 for providing substantial mechanical advantage by the use of a small allen wrench. Consequently, the use of large wrenches, such as used for tightening seals in known liquid chromatography equipment, is avoided. The substantial mechanical advantage enables effective elimination of voids and channels in packing material 202 and 204, for example.

The embodiment of compressing means 270 shown in FIG. 5 can be substituted for either one or both of the end caps 174 and 176 and end fittings 198 and 200 shown in FIG. 2. Typically, however, the compressing means 270 shown in FIG. 5 is substituted for only one of the end caps 174 and 176 and end fittings 198 and 200 shown in FIG. 2.

Compressing means 270 can also be incorporated into the column apparatus shown in FIG. 4. End cap 272 is substituted for end cap 262, and housing 274 and tubing 319 are substituted for end fitting 248. Additionally, seal retainer 275 is substituted for the seal retainer in the enclosing means (not shown) of first end portion 244 of tube 242.

A slight modification of end cap 256 is needed in the case where compressing means 270 is incorporated into the column apparatus shown in FIG. 4. With reference to FIG. 4, rim 312 is internally threaded for threadable connection with threaded portion 258 of end cap 256 shown in FIG. 4. In order to provide a modular structure for use with the embodiments of the column apparatus shown in FIGS. 2 and 4, it is preferable that the length of end cap 256 be extended as needed for engagement with rim 312, rather than providing an extended rim 312 for engagement with end cap 256 as might appear to be needed in view of FIG. 4. An extended rim 312 can, however, be provided instead. In any event, the operation in the case of the embodiment shown in FIG. 4 is substantially the same as described above with reference to FIG. 2.

Incorporation of compressing means 270 into column apparatus 10 shown in FIG. 1 preferably incorporates various economizing modifications, as shown in FIG. 6. Column apparatus 10B partially depicted in FIG. 6 is particularly useful in the case of large diameter column apparatus 10B, for example, where tube 12 has an inside diameter on the order of 41.4 millimeters.

Referring to FIGS. 1 and 6, end cap 272, housing 274, and tubing 319 are substituted for end fitting 42. Furthermore, seal retainer 275, preferably in combination with a frit filter 336, is substituted for seal retainer 24. Ferrule 322 is threadably engaged with seal retainer 275 as shown in FIG. 6.

Seal 54 is disposed in seal region 334. Seal retainer 275 and stopper 22 are included in end-to-end configuration and comprise modified plugging means 20' included in first end portion 16 of tube 12. Plugging means 20' is movable along the inside surface 26 of tube 12.

Additionally, urging means 337 including connecting means 338 is substituted for cylindrical member 74 and end cap 82. Connecting means 338 includes a first threaded end portion 339 and a second threaded end portion 340. Rim 312 is preferably also externally threaded for threaded engagement with first threaded end portion 339 of connecting means 338 for attaching compressing means 270 to column apparatus 10B. Second threaded end portion 340 of connecting means 338 threadably engages threaded first end portion 84 of second tube 62 for interconnecting tube 12 with second tube 62.

Although coupler 100 and enclosing means 90 and 120 can be retained, fluid interconnecting means 342 is preferably substituted for coupler 100 and seal retainers 96 and 132. Fluid interconnecting means 342 includes a core 344 having a passage 346, as well as a first end portion 348 and a second end portion 350 having a reduced diameter, as shown in FIG. 6. A first seal retaining cap 352 is mounted to first end portion 348 by means of screws 352 inserted through countersunk bores 356 in first seal retaining cap 352 and threadably engaged in threaded wells 358 in core 344 for retaining seal 56. Similarly, a second seal retaining cap 360 is mounted to second end portion 350 by means of screws 354 inserted through countersunk bores 362 in second seal retaining cap 360 and threadably engaged in threaded wells 364 in core 344 for retaining seal 58. A frit filter 366 can be positioned adjacent second seal retaining cap 360.

The remainder of column apparatus 10B shown in FIG. 6 can correspond to column apparatus 10 shown in FIG. 1. Also, the above description of FIG. 3 also relates to column apparatus 10B shown in FIG. 6, as well as to column apparatus 10 shown in FIG. 1.

In operation, plugging means 20', stopper 94, fluid interconnecting means 342, and filter 366 are inserted in tube 12 and second tube 62. Next, connecting means 338 is attached to tube 62. Then, compressing means 270 is attached to connecting means 338.

Thereafter, an allen wrench (not shown) is employed for operating compressing means 270 as described above in connection with FIG. 2 for applying axial force to plugging means 20' which compresses packing material 14. The axial force is also transferred through urging means 337, tube 62 and its associated elements, filter 366, fluid interconnecting means 342, and stopper 94 to packing material 14 adjacent stopper 94 in tube 12, as well as through packing material 14, stopper 94, fluid interconnecting means 342, filter 366, and stopper 128 to packing material 80 within second tube 62 adjacent stopper 128 due to the connection between urging means 337 and tube 62. Axial force would also be transferred through plugging means 20', packing material 14, stopper 94, fluid interconnecting means 342, filter 366, and stopper 128 to packing material 80 and opposed by connecting means 338, bushing 180, end cap 144, end fitting 142, and enclosing means 140 for compressing packing material 80 if connecting means 338 were connected to bushing 180 instead of tube 62. In view of the mechanical advantage provided by compressing means 270 as described in connection with FIG. 2, packing material 14, as well as packing material 80, is compressed for eliminating voids and channels.

While the foregoing embodiments of the present invention have been set forth in considerable detail for the purposes of making a complete disclosure of the invention, it may be apparent to those of skill in the art that numerous changes may be made in such detail without departing from the spirit and principles of the invention as embraced by the claims below.

What is claimed is:

1. In a liquid chromatography column apparatus utilizing a material for separating constituents comprising a tube filled with said material, said tube having a first end portion and a second end portion, means for plugging said first end portion of said tube, said plugging means including a passage therethrough, said plugging means fitting adjacent said material within said tube and being movable within said tube, an end fitting having a portion placed within said tube adjacent said plugging means, said end fitting including a passage therethrough which communicates with said passage of said plugging means, means for sealing a portion of the inside of said tube between said tube and said end fitting, and means for enclosing said second end portion of said tube, said enclosing means including a passage therethrough from the exterior of said tube to the interior thereof, the improvement comprising:

compressing means incorporated into said end fitting in said first end portion of said tube for applying axial force to said plugging means, said compressing means having a mechanical advantage for applying said axial force to said plugging means, thereby compressing said material so as to eliminate voids and channels in said material within said tube.

2. The column apparatus of claim 1 wherein said tube is a first tube, said column apparatus further comprising a second tube filled with a material, said second tube having first and second end portions, and first and second means for enclosing said first and second end portions, respectively, a coupler including an element having a first portion fitting and being movable within said second end portion of said first tube, said element further having a second portion fitting and being movable within said first end portion of said second tube, said second tube including first and second passages through said first and second enclosing means, respectively, which communicate with said material within said second tube, said element including a passage therethrough communicating with said first passage of said first enclosing means of said first end portion of said second tube and with said passage of said enclosing means of said second end portion of said first tube.

3. The column apparatus of claim 2 wherein said coupler further comprises means for retaining said first and second portions of said element within said first end portion of said second tube and within said second end portion of said first tube, respectively.

4. The column apparatus of claim 2, said column apparatus further comprising means for urging said element against said enclosing means of said second end portion of said first tube.

5. The column apparatus of claim 2, said column apparatus further comprising means for connecting said compressing means to said second tube for urging said element against said first enclosing means of said first end portion of said second tube, thereby compressing said material in said second tube.

6. In liquid chromatography column apparatus utilizing a material for separating constituents comprising a tube filled with said material, said tube having a first end portion, a second end portion, and an inside surface, first means for enclosing said first end portion of said tube, said first enclosing means for said first end portion of said tube including a passage therethrough which communicates with said material within said tube, said first enclosing means for said first end portion of said tube having at least a part within said tube and being movable within said tube, second means for enclosing said second end portion of said tube, said second enclosing means for said second end portion of said tube including a passage therethrough communicating with said material within said tube, said second enclosing means for said second end portion of said tube having at least a part within said tube, said material being positioned between said first and second enclosing means, means for sealing a portion of the inside of said first and second end portions of said tube between said first and second enclosing means and said inside surface of said tube, and means for retaining said parts of said first and second enclosing means within said tube, the improvement comprising:

compressing means incorporated into said first end portion of said tube for applying axial force with mechanical advantage to said first enclosing means, thereby moving said first enclosing means toward said material within said tube.

7. The column apparatus of claim 6, said column apparatus further comprising meas for urging said second enclosing means toward said material within said tube.

8. Apparatus for facilitating compression of packing material in a liquid chromatography column apparatus, comprising:

a housing adapted to be selectively attached to said column apparatus, said column apparatus containing said material;

gear means contained in said housing;

an end cap secured to said housing; and tubing, associated with said housing, gear means, and end cap, adapted for connection in fluid communication with a passage in movable plugging means incorporated in an end portion of said tube adjacent said material, said passage being in fluid communication with said material;

said gear means being actuatable when said housing is attached to said column apparatus for applying an axial force to said plugging means for moving said plugging means toward said material;

thereby compressing said material.

9. The apparatus of claim 8 wherein said housing has a threaded rim adapted for threaded engagement with a threaded end portion of said tube.

10. The apparatus of claim 8 wherein said housing has a threaded rim adapted for threaded engagement with a threaded end cap associated with an end fitting at a distal end of said tube.

11. The apparatus of claim 8 wherein said gear means comprises:

a pinion gear rotatably mounted in said housing;

a spindle threadably engaged in a threaded bore in said housing; and a drive gear mounted on said spindle, said drive gear being in mesh with said pinion gear;

said pinion gear being actuable through said end cap;

said pinion gear being rotatable to impart rotation to said drive gear; and said rotation imparted to said drive gear being transferred to said spindle for extending said spindle in said housing for contacting said plugging means, thereby moving said plugging means toward said material.

12. The apparatus of claim 11 wherein said pinion gear includes a base portion and a gear portion, said base portion being rotatable in a bore in said housing, said pinion gear having a threaded well aligned with a bore in said end cap, said apparatus further comprising an allen bolt inserted through said bore in said end cap and threadably engaged in said threaded well in said pinion gear, whereby rotation imparted to said allen bolt imparts rotation to said pinion gear.

13. The apparatus of claim 11 wherein said end cap has a central bore, said drive gear has a central bore, and said spindle has a central bore, said central bores of said end cap, drive gear, and spindle being aligned, said tubing being disposed in said central bores of said end cap, drive gear, and spindle. said tubing having a threaded ferrule adapted to be threadably engaged with said plugging means so that said tubing is in fluid communication with said passage.

14. The apparatus of claim 11 wherein said pinion gear has a smaller diameter than said drive gear so as to provide mechanical advantage.

15. The apparatus of claim 8 wherein said tubing has a threaded ferrule adapted to be threadably engaged with said plugging means so that said tubing is in fluid communication with said passage.

16. The apparatus of claim 8 wherein said gear means provides mechanical advantage.

17. A method for facilitating compresion of packing material in a liquid chromatography column apparatus, comprising the steps of:

providing compressing means, the compressing means being selectively attachable to the column apparatus, the compressing means including a gear means;

attaching the compressing means to the column apparatus, the column apparatus including a tube containing the material and movable plugging means adjacent the material; and actuating the gear means when the compressing means is attached to the column apparatus;

whereby the gear means applies an axial force for moving the plugging means toward the material.

18. The method of claim 17 wherein the compressing means has a threaded rim and the tube has a threaded end portion and the step of attaching the compressing means to the column apparatus comprises threadably engaging the threaded rim of the compressing means with the threaded end portion of the tube.

19. The method of claim 17 wherein the compressing means has a threaded rim and the column apparatus has a threaded end cap associated with an end fitting at a distal end of the tube and the step of attaching the compressing means to the column apparatus comprises threadably engaging the threaded rim of the compressing means with the threaded end cap.

20. The method of claim 17 wherein the step of actuating the gear means provides mechanical advantage.

* * * * *